United States Patent [19]

Auerbach et al.

[11] Patent Number: 4,570,001

[45] Date of Patent: Feb. 11, 1986

[54] PROCESS FOR SYNTHESIZING CERTAIN N-BENZOYLAMINO INDOLINES

[75] Inventors: Joseph Auerbach, Brooklyn; Martin Kantor, Mamaroneck, both of N.Y.

[73] Assignee: Science Union et Cie, Suresnes, France

[21] Appl. No.: 604,405

[22] Filed: Apr. 27, 1984

Related U.S. Application Data

[63] Continuation of Ser. No. 439,452, Nov. 5, 1982, abandoned, which is a continuation-in-part of Ser. No. 219,416, Dec. 22, 1980, abandoned.

[51] Int. Cl.[4] .......................................... C07D 209/04
[52] U.S. Cl. ...................................... 548/483
[58] Field of Search ...................................... 548/483

[56] References Cited

PUBLICATIONS

Hyre, J. E. et al., J. Amer. Chem. Soc., 80, 437–439, (1958).
W. Houlihan, Indoles (Part I), 472–473, John Wiley and Sons, NY (1972).
M. Schmid et al., Helv. Chim. Acta, 56, No. 3–4, 105–124 (1973).
A. Bader et al., J. Amer. Chem. Soc. 83, 3319–3323 (1961).

Primary Examiner—George F. Lesmes
Assistant Examiner—S. A. Gibson
Attorney, Agent, or Firm—Gordon W. Hueschen

[57] ABSTRACT

Compounds of the structure

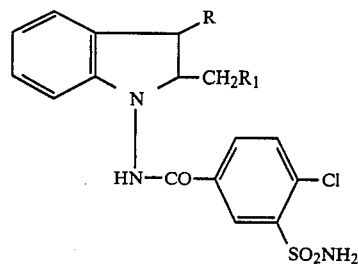

wherein R is hydrogen, lower alkyl containing 1 to 5 carbon atoms, cycloalkyl containing 3 to 7 carbon atoms, phenyl or phenyl substituted with halogen, trifluoromethyl, or lower alkyl or lower alkoxy having 1 to 4 carbon atoms and $R_1$ is hydrogen, lower alkyl having 1 to 4 carbon atoms, phenyl or phenyl lower alkyl wherein the lower alkyl has 1 to 4 carbon atoms, are formed by cyclizing a compound of the structure

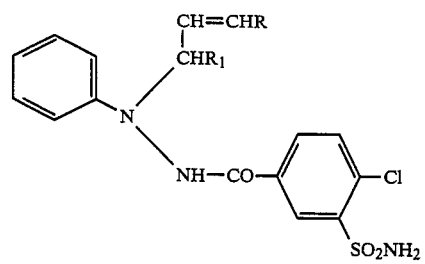

wherein R and $R_1$ are as defined above, in the presence of an acid.

10 Claims, No Drawings

PROCESS FOR SYNTHESIZING CERTAIN N-BENZOYLAMINO INDOLINES

This application is a continuation of application Ser. No. 439,452, filed Nov. 5, 1982, and now abandoned, which has a continuation-in-part of application Ser. No. 219,416, filed Dec. 22, 1980, now abandoned.

The present invention relates to pharmaceutically active compounds. It particularly relates to an improved process for the preparation of indolines having anti-hypertensive activity.

Indolines of the formula

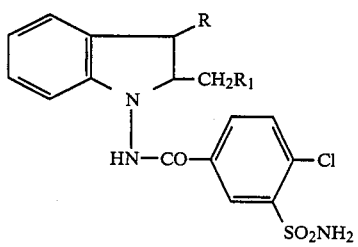

wherein R is hydrogen, lower alkyl containing 1 to 5 carbon atoms, cycloalkyl containing 3 to 7 carbon atoms, phenyl and phenyl substituted by halogen, trifluoromethyl, and lower alkyl and lower alkoxy having 1 to 4 carbon atoms, and $R_1$ is hydrogen, lower alkyl, phenyl, and phenyl lower alkyl are disclosed in U.S. Pat. No. 3,565,911 (the '911 patent) as having potent antihypertensive activity.

The method for the preparation of these compounds, as disclosed in the '911 patent, involves a multistep process starting with the nitrosation of an indoline appropriately substituted in the 2-position to provide an N-nitroso derivative, followed by the reduction of the nitroso group to give an N-amino-indoline, and the reaction of this compound with 3-sulfamyl-4-chlorobenzoyl chloride to give the desired end products.

The yields in these reactions are poor and the synthesis involves the preparation of nitrosamines, compounds which have been reported to be carcinogenic.

It is, accordingly, an object of the present invention to provide a convenient process for the preparation of isoindolines of structure I above.

The present invention when carried out with a suitable acid provides the desired cyclized molecule in high yield, even with relatively weak acids such as orthophosphoric acid and even at relatively mild reaction conditions. By contrast, the literature shows that non-analogous, much simpler N-allyl anilines, substituted with —H or —CH$_3$ on the nitrogen atom, react under relatively harsh conditions of temperature and acid strength to provide a cyclized molecule in relatively mediocre yield together with a number of by-products. This literature does not suggest that starting material in the present process will cyclize at all, let alone that it will do so in good yield and even under mild conditions.

In accordance with the present invention, isoindolines of structure I above are prepared by the cyclization of a compound of the structure

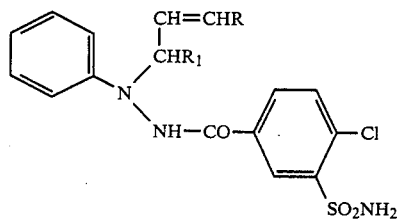

wherein R and $R_1$ are as previously defined, in the presence of a suitable Lewis or Bronsted acid or mixtures thereof. Preferably, R and $R_1$ are independently H or lower alkyl having up to 6 carbon atoms.

Examples of suitable acids include alkyl-sulfonic acids and halogen-substituted-alkyl-sulfonic acids, wherein the alkyl group has 1 to 4 carbon atoms; aryl sulfonic acids wherein the aryl ring is unsubstituted or substituted with halogen, methyl, or ethyl, such as p-toluenesulfonic acid; polymeric resin sulfonic acids, such as polystyrene resins cross-linked with up to about 5% divinyl benzene and substituted with sulfonic radicals, in the (H+) form; hydrochloric acid; sulfuric acid; and phosphoric acid, by which term is meant not only orthophosphoric acid but also polyphosphoric acids of the general formula $H_{n+2}P_nO_{3n+1}$ and having the general structure

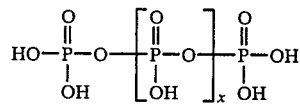

where X is zero (pyrophosphoric acid) to about 20 or 25. Commercial polyphosphoric acid generally has a composition corresponding to 80–85% $P_2O_5$. Hydrochloric acid should be used in conjunction with a reaction-promoting effective amount of zinc chloride or an equivalent catalyst, such as about 0.5 to about 2.5 grams (preferably 1 to 2 grams) of zinc chloride per milliliter of concentrated hydrochloric acid.

Of the above-listed acids, the preferred acids are alkylsulfonic, halogen-substituted-alkyl sulfonic, aryl sulfonic, resin sulfonic, and phosphoric acids and hydrochloric acid used in conjunction with a reaction-promoting effective amount of zinc chloride. The most preferred acids are methanesulfonic, trifluoromethanesulfonic, phosphoric (orthophosphoric and polyphosphoric) acids, and hydrochloric acid containing about 0.5 to about 2.5 grams of zinc chloride per milliliter of concentrated hydrochloric acid.

The cyclization is preferably carried out by heating the compound of structure II and the acid in an inert solvent at a temperature of about 20° C. to 100° C. Suitable inert solvents include water, polyhalogenated hydrocarbons, higher boiling ethers and glycol ethers. The cyclization reaction proceeds to completion within a length of time generally ranging from about half an hour to about six hours.

The compounds of structure II may readily be obtained by treatment of a compound of the structure

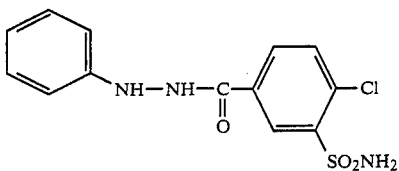

with an allyl halide of the structure

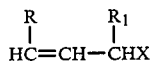

wherein X is halogen, preferably bromine, and R and $R_1$ are as previously defined and, as noted above, are preferably independently hydrogen and lower alkyl.

The hydrazide, III, is readily obtained by treating phenylhydrazine with 3-aminosulfonyl-4-chlorobenzoyl chloride.

The invention will be more fully illustrated in the examples which follow. These examples are given by way of illustration and are not to be considered as limiting.

EXAMPLE I

1-Allyl-1-phenyl-2(3-sulfamoyl-4-chlorobenzoyl)-hydrazine

A mixture of 3-aminosulfonyl-4-chloro-benzhydrazide (326.6g, 1.0 mole) sodium bicarbonate (420.0g, 2.0 mole), potassium iodide (16.6g, 0.1 mole) and allyl bromide (242.0g, 2.0 mole) in isopropanol (1,500 ml) was stirred at gentle reflux for 20 hours, then cooled to 50° and filtered by suction. The cake was washed twice with 100 ml portions of isopropanol. The washes and filtrate were combined and diluted with sufficient water to make a 70% isopropanol solution, then allowed to stir overnight to complete crystallization. The crude product was filtered and washed twice with 100 ml portions of isopropanol-water (70:30). One recrystallization from isopropanol-water (70:30) and clarification with activated charcoal gave pure compound in 80% yield.

EXAMPLE II 1-(4-Chloro-3-sulfamoylbenzamido)-2-methylindoline

A mixture of 1-allyl-1-phenyl-2-(3-sulfamoyl-4-chlorobenzoyl)-hydrazine (36.6g, 0.1 mole) and orthophosphoric acid, 85% (100 ml) was stirred at 60° for a period of 4 hours. Dilution with water gave crude 1-(4-chloro-3-sulfamoylbenzamido)-2-methylindoline which was purified by recrystallization from isopropanol-n-hexane (60:40).

EXAMPLE III 1-(4-Chloro-3-sulfamoylbenzamido)-2-methylindoline

In a 50 ml reaction vessel was placed 1 gram (2.73 mmols) of 1-allyl-1-phenyl-2-(3-sulfamoyl-4-chlorobenzoyl)-hydrazine and 10 ml of trifluoromethane sulfonic acid. The reaction mixture was stirred under a nitrogen atmosphere at ambient temperatures. After 15 minutes the solid dissolved and the reaction was allowed to proceed for a total of 4.75 hours. The reaction mixture was worked up by pouring the acid solution into 250 ml of water, extracting the precipitate into ethyl acetate, washing the ethyl acetate several times with water and sodium bicarbonate solution. The ethyl acetate phase was separated and dried with magnesium sulfate and clarified. The isolated product was further purified by dry column chromatography and then crystallized from 50% w/w methanol-acetone.

EXAMPLE IV 1-(4-Chloro-3-sulfamoylbenzamido)-2-methylindoline

In a 50 ml round bottom was placed 8 grams of Lucas reagent. The reagent is prepared by dissolving 16 grams of anhydrous zinc chloride in 10 ml of concentrated hydrochloric acid. To this reagent was added 100 mg (0.27 mmols) of 1-allyl-1-phenyl-2-(3-sulfamoyl-4-chlorobenzoyl)-hydrazine with stirring under nitrogen for a short time to dissolve the solid. The reaction cyclized at 60° C. over 6 hours. The reactant was worked up by pouring the cooled reaction mixture into water and extracting the product into ethyl acetate. The ethyl acetate phase was cross washed several times with water and sodium bicarbonate solution. The ethyl acetate solution is dried with magnesium sulfate, clarified and evaporated to dryness yielding 84 mg of crude 1-(4-chloro-3-sulfamoylbenzamido)-2-methylindoline.

EXAMPLE V

1-Crotyl-1-phenyl-2-(3-sulfamoyl-4-chlorobenzoyl)hydrazine

In a 250 ml round bottomed flask is placed 90 ml of N,N-dimethylformamide and 30 grams (0.092 mole) of 3-amino sulfonyl-4-chlorobenzhydrazide. The mixture was stirred to dissolve the solid, then 18.63 gms (0.138 mole) of crotyl bromide were added. The mixture was heated at 100° for 1.66 hours at which point TLC showed the reaction to be complete. The reaction mixture was cooled and diluted with 200 ml isopropanol. This solution was dripped into a slurry of 1.5 liters of ice and 4 liters of water. The solid which precipitated was collected, washed with water and air dried overnight, yielding the product which could be recrystallized from chloroform/carbon tetrachloride.

The compound gave the correct mass spectrum NMR and CMR analysis. Carbon magnetic resonance shows cis/trans relative ratio of the crotyl side chain to be approximately 10:90.

EXAMPLE VI 1-(4-Chloro-3-sulfamoylbenzamido)-2,3-dimethyl indoline 1.97 mmol (0.0175 g) 1-crotyl-1-phenyl-2-[(3-sulfamoyl-4-chlorobenzoyl)]-hydrazine was mixed with 15 ml of orthophosphoric acid and kept at 100° C. for 45 minutes at which point thin layer chromatography showed that starting material was consumed. The mixture was cooled and poured into water, 40 ml, and extracted with ethyl acetate, 40 ml, 2 times. The ethyl acetate was cross washed with water, then 1 mole sodium bicarbonate, then brine. The ethyl acetate solution was dried and the solution taken to dryness. The residue was filtered through silica gel, eluting with ethyl acetate-hexane and the eluent was taken to dryness giving the product. The structure is supported by a mass spectrum and NMR analysis.

EXAMPLE VII

1-(4-chloro-3-sulfamoylbenzamido)-2-methylindoline

In a 250 ml round bottom reaction flask was placed 2 grams (5.47 mmol) of (1-allyl-1-phenyl-2-(3-sulfamoyl-4-chlorobenzoyl)-hydrazine and to this was added 36 grams of polyphosphoric acid (commercial grade, 83%±2% $P_2O_5$). The mixture was placed in a 100°-105° C. oil bath. At this temperature the mixture was stirable and the solid dissolved. After a total time of 45 minutes reaction time, (30 minutes at 100°-105° C. and 15 minutes to cool to 45° C.), 72 grams of crushed ice was added to the reaction mixture. The milky slurry which formed was diluted to 400 ml with water and was extracted with ethyl acetate. The ethyl acetate layer was washed successively with water until it was neutral, then once with 1 molar sodium bicarbonate solution and once with brine solution. The ethyl acetate phase was dried with magnesium sulfate and clarified. The ethyl acetate phase was vacuum evaporated to dryness and the residue was placed under high vacuum. The recovered product was 1.26 grams (63% yield). The product was shown to be 1-(4-chloro-3-sulfamoylbenzamido)-2-methylindoline by spectroscopic means and thin layer chromatography.

We claim:

1. A process for the preparation of a compound of the structure

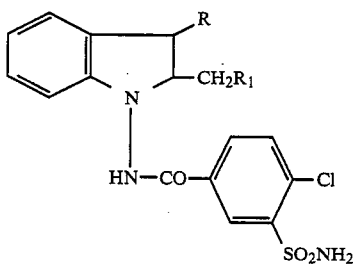

wherein R is hydrogen, lower alkyl containing 1 to 5 carbon atoms, cycloalkyl containing 3 to 7 carbon atoms, phenyl or phenyl substituted with halogen, trifluoromethyl, or lower alkyl or lower alkoxy having 1 to 4 carbon atoms and $R_1$ is hydrogen, lower alkyl having 1 to 4 carbon atoms, phenyl or phenyl lower alkyl wherein the lower alkyl has 1 to 4 carbon atoms, which comprises cyclizing a compound of the structure

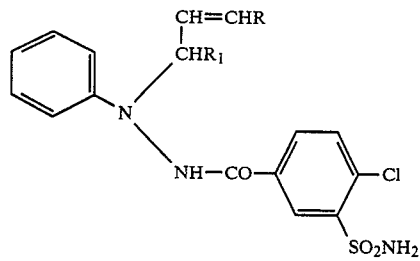

wherein R and $R_1$ are as defined above, in the presence of an acid selected from the group consisting of alkyl and halogen-substituted-alkyl sulfonic acids, wherein the alkyl group has 1 to 4 carbon atoms; aryl sulfonic acids wherein the aryl ring is unsubstituted or substituted with halogen, methyl, or ethyl; polymeric resin sulfonic acids in the (H+) form; hydrochloric acid; and phosphoric acid.

2. A process according to claim 1 wherein the acid is selected from the group consisting of hydrochloric acid containing a reaction-promoting effective amount of zinc chloride, and methanesulfonic, trifluoromethanesulfonic, and phosphoric acids.

3. A process according to claim 2 wherein R and $R_1$ are independently hydrogen and lower alkyl.

4. A process according to claim 3 wherein R is hydrogen.

5. A process according to claim 4 wherein $R_1$ is hydrogen or an alkyl group having 1 to 4 carbon atoms.

6. A process according to claim 5 wherein $R_1$ is hydrogen.

7. A process according to claim 6 wherein the acid is orthophosphoric acid.

8. A process according to claim 2 wherein the acid is orthophosphoric acid.

9. A process according to claim 1 wherein the cyclizing is carried out at a temperature of about 20° C. to 100° C.

10. A process according to claim 2 wherein the cyclizing is carried out at a temperature of about 20° C. to 100° C.

* * * * *

UNITED STATES PATENT AND TRADEMARK OFFICE
CERTIFICATE OF CORRECTION

PATENT NO. : 4,570,001

DATED : February 11, 1986

INVENTOR(S) : Joseph Auerbach and Martin Kantor

It is certified that error appears in the above-identified patent and that said Letters Patent is hereby corrected as shown below:

Col. 1, line 7; "has" should read -- was --

Signed and Sealed this

Eighth Day of July 1986

[SEAL]

Attest:

Attesting Officer

DONALD J. QUIGG

Commissioner of Patents and Trademarks